United States Patent

Sigworth

Patent Number: 5,345,808
Date of Patent: Sep. 13, 1994

[54] GAS ANALYZER FOR MOLTEN METALS

[76] Inventor: Geoffrey K. Sigworth, 321 Tioga St., Johnstown, Pa. 15905

[21] Appl. No.: 113,344

[22] Filed: Aug. 30, 1993

[51] Int. Cl.$^5$ ............................................. G01N 7/10
[52] U.S. Cl. ................................................ 73/19.07
[58] Field of Search ...................................... 73/19.07

[56] References Cited

U.S. PATENT DOCUMENTS

| | | | |
|---|---|---|---|
| 2,861,450 | 11/1958 | Ransley | 73/19.07 |
| 4,239,532 | 12/1980 | Allersma et al. | 75/93 |
| 4,454,748 | 6/1984 | Terai et al. | 73/19.07 |
| 4,624,128 | 11/1986 | Pelton | 73/19.07 |
| 4,757,707 | 7/1988 | Harvey et al | 73/19.07 |
| 4,878,375 | 11/1989 | Roggen | 73/19.07 |
| 4,907,440 | 3/1990 | Martin et al. | 73/19.07 |

FOREIGN PATENT DOCUMENTS

| | | |
|---|---|---|
| 0435365 | 3/1991 | European Pat. Off. . |
| 148342 | 7/1986 | Japan ................ 73/19.07 |
| 684865 | 12/1952 | United Kingdom ......... 73/19.07 |

OTHER PUBLICATIONS

E. Fromm, "Determination of the Hydrogen Concentration in Aluminum Melts by Continuous Measurement of the Hydrogen Equilibrium Pressure", Aluminum, 65 (1989). No. 12, pp. 1240–1243.

C. E. Ransley et al, "An Instrument for Measuring the Gas Content of Aluminum Alloys During Melting and Casting", Journal of the Institute of Metals, 1957–58, vol. 86, pp. 212–219.

*Primary Examiner*—Hezron E. Williams
*Assistant Examiner*—Joseph W. Roskos
*Attorney, Agent, or Firm*—Andrew Alexander

[57] ABSTRACT

Disclosed is a probe for determining the gas content of molten metal. The probe comprises a porous filter head permeable to gas and impermeable to the molten metal and a hollow cast iron tube or sleeve having an upper portion and a lower portion, the sleeve or tube attached to the filter head at the lower portion. A small diameter tube may be positioned in the sleeve, or the cast iron tube may be formed to provide a small diameter bore. Means for drawing a vacuum on the tube and means for measuring gas pressure in the tube is provided.

16 Claims, 3 Drawing Sheets

GAS ANALYZER FOR MOLTEN METALS

INTRODUCTION

This invention relates to molten metals, and more particularly, it relates to an apparatus and method for the direct measurement of the level of gas in a molten metal.

There has been a great interest in accurately determining the level of gas dissolved in a molten metal because dissolved gas can result in the formation of holes or cracks in the ingot cast therefrom. In aluminum, for example, hydrogen has a much greater solubility in the molten metal than in the solid form. That is, hydrogen is almost twenty times more soluble in molten aluminum than in solid aluminum. Thus, when molten aluminum freezes gas present in the melt prior to solidification is rejected by the solid and accumulates in the remaining liquid until the concentration of dissolved gas becomes sufficiently large to form gas bubbles or pores. Because of this problem, it is important to be able to accurately and quickly determine the level of hydrogen dissolved in the molten aluminum, and whether further degassing is necessary. In addition, it is important to know when the level of hydrogen has reached an acceptable level in order to optimize the casting process, and avoid unnecessary costs associated with casting.

Many methods have been suggested and tried to measure the level of gases in molten metal. However, these methods are either too time consuming or they utilized equipment which is too fragile. It will be understood that it is important to obtain the results of the gas measurement quickly, accurately and continuously in order to maintain control of the degassing process. Further, it will be understood that fragile equipment merely leads to erroneous results.

There are two general methods for measuring dissolved gas in molten metal. In the first of these methods, a stream of inert gas is introduced into and collected from the molten metal. This gas stream is recirculated by pumping many times through the metal until the partial pressure of dissolved gas in the recirculating inert gas bubbles is the same as the partial pressure of dissolved gas in the liquid metal. This technique is described in detail by Ransley in U.S. Pat. No. 2,861,450. However, this method tends to be cumbersome and slow, and the equipment required for recirculating the inert gas is costly. Various improvements have been proposed for this method of analysis (see U.S. Pat. Nos. 4,454,748, 4,624,128, 4,757,707, and 4,907,440) but they still do not solve all the problems inherent in this procedure The second method, referred to herein as the direct pressure measurement method, does not use recirculating gas bubbles, but instead utilizes a probe having a porous tip which permits dissolved gas to pass through but does not permit molten metal to pass. This method was disclosed by C. E. Ransley, et al. in an article entitled "An Instrument for Measuring the Gas Content of Aluminum During Melting and Casting of Aluminum" published in the Journal of the Institute of Metals, Vol. 86, pp. 212-219 (1957-1958). Ransley et al. showed that the direct pressure method can give reliable and accurate gas measurements. However, because of the complex diffusion membrane required, it was concluded that the method was not practical. Thus, although established in principle 35 years ago, the direct pressure measurement method of gas analysis has not become a viable commercial technique because of problems associated with the probe assembly that contacts the molten metal.

A direct pressure measurement device is disclosed by E. Fromm in an article entitled "Determination of the Hydrogen Concentration in Aluminum Melts by Continuous Measurement of the Hydrogen Equilibrium Pressure", published in Aluminum Vol. 65, (1989). The article notes that the main problem in building an analyzer is the selection of suitable materials for the part of the probe or sensor submerged in the melt. The probe consists of a tube with a porous tip. The article notes that the tube must not react with the melt or must react only slowly and must be resistant to thermal shock. Further, the article suggests the use of alumina tubes because they have long-term stability and adequate resistance to thermal shock. However, the article notes that the alumina tubes must be handled carefully, particularly when lowered into the hot melt. The article notes that metal tubes are not suitable unless used only briefly.

To create a thermal shock-resistant article, Allersma et al. U.S. Pat. No. 4,239,532 discloses a unitary probe having the porous end thereof formed by leaching. This patent suggests that the probe be fabricated from ceramic composites of mullite and silica or alumina and silica and that the material selected for the probe must be leachable. However, this severely limits the materials that may be employed. Another disadvantage of this probe was the very slow response time.

Roggen U.S. Pat. No. 4,878,375 discloses a probe for measuring hydrogen in aluminum melts, and indicates that the capillary tube is preferably made from alumina or that metallic capillary tubes, e.g., steel or nickel tubes plasma coated with aluminum oxide, can also be employed. However, the patent discloses the use of a graphite porous tip or calcined material not wet by the melt.

EP 0 435 365 A1 discloses a probe for measuring hydrogen in molten aluminum. The probe employs a porous aluminum oxide tube that is welded onto the end of a stainless steel tube. A tube of aluminum surrounds the probe. The outer aluminum tube melts upon immersion in the melt. According to the reference, this alleviates thermal shock. According to the inventors, for best results the assembly must be preheated for 24 hours prior to immersion in liquid metal. However, this probe would seem to be costly to produce and be inconvenient to use.

It will be seen that there is still a great need for an improved analyzer that employs a probe that is resistant to thermal shock, easy to use, inexpensive to manufacture, and that is rugged and reliable when used on the floor of the casting plant. The present invention provides such a probe.

SUMMARY OF THE INVENTION

It is an object of the invention to provide an improved gas analyzer for molten metal.

It is another object of the invention to provide an improved gas analyzer to determine the amount of hydrogen dissolved in molten aluminum.

It is still another object of the invention to provide an improved analyzer which utilizes a probe comprised of a combination metal tube and porous filter member.

Still, it is another object of the invention to provide an improved analyzer which utilizes a probe comprised of a cast iron tube and a porous filter member.

And still, it is another object of the invention to provide an improved analyzer which utilizes a probe comprised of a cast iron tube having a protective coating thereon resistant to attack by molten metal and porous member on one end thereof permeable by gas and impervious to molten metal These and other objects will become apparent from a reading of the specification and claims appended hereto.

In accordance with these objects, there is provided a hollow probe for immersion in a molten metal for determining the gas content thereof by drawing a vacuum on the probe and permitting gas to permeate from the molten metal and equilibrate in the probe, wherein gas pressure can be measured to determine the gas pressure in the molten metal. The probe comprises a porous filter head permeable to gas and impermeable to the molten metal, and a hollow cast iron tube or sleeve having an upper portion and a lower portion, the sleeve or tube attached to the filter head at the lower portion. A small diameter tube may be positioned in the sleeve or the cast iron tube may be formed to provide a small diameter bore. When a small diameter tube is employed, it has a first end that extends to the lower portion of the sleeve adjacent to the filter head and another or second end attached to means for drawing a vacuum on the tube and means for measuring gas pressure in the tube. When the cast iron tube is employed having a small diameter bore, then the upper portion of the cast iron tube can be attached to the vacuum means or gas pressure measuring device.

DETAILED DESCRIPTION OF PREFERRED EMBODIMENTS

Figure 1:
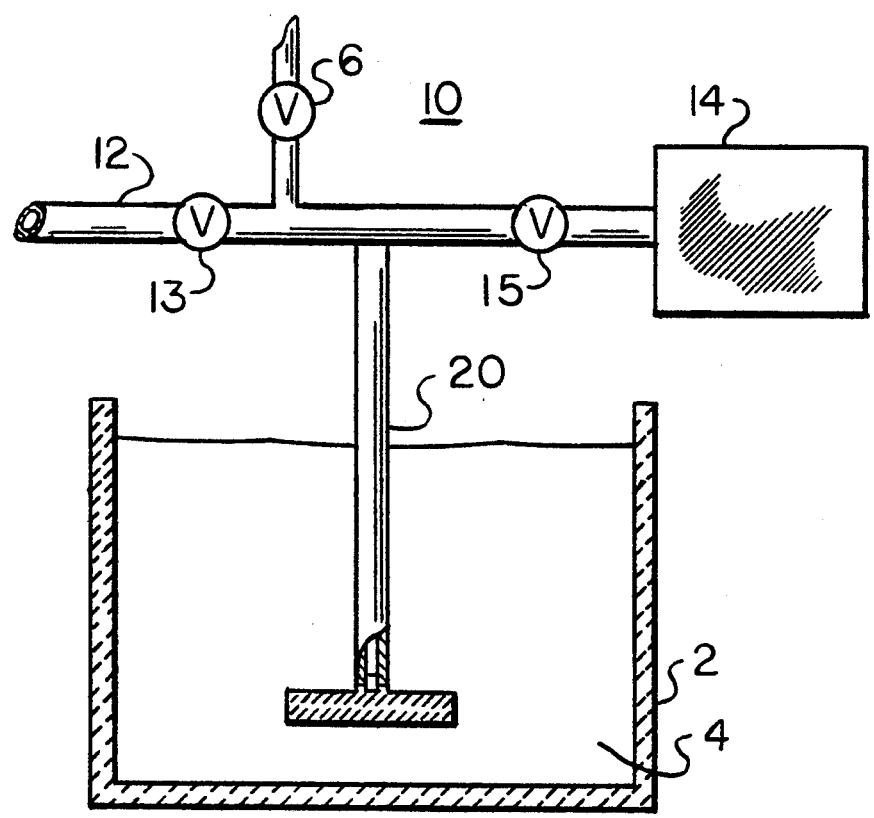
FIG. 1 is a schematic of a gas analyzer in accordance with the invention.

Referring now to FIG. 1, there is shown a schematic of an analyzer 10 having a probe 20 provided in a tank 2 of molten metal 4. Further, the analyzer comprises a vacuum means 12 and gas pressure analysis means 14. Means 6 can be provided for doping probe 20 to improve gas diffusion response time. The molten metal for which the analyzer is used can be any molten metal where it is desired to determine the amount of gas, such as hydrogen, nitrogen or oxygen, in the molten metal. In general, a vacuum is applied to probe 20, and then a period of time is allowed for gas in the molten metal to diffuse through the porous filter head into the probe until equilibrium is reached. Then, the level of gas from the melt is measured by the gas pressure analysis means. In this way, the level of gas in the molten metal is determined.

Figure 2:
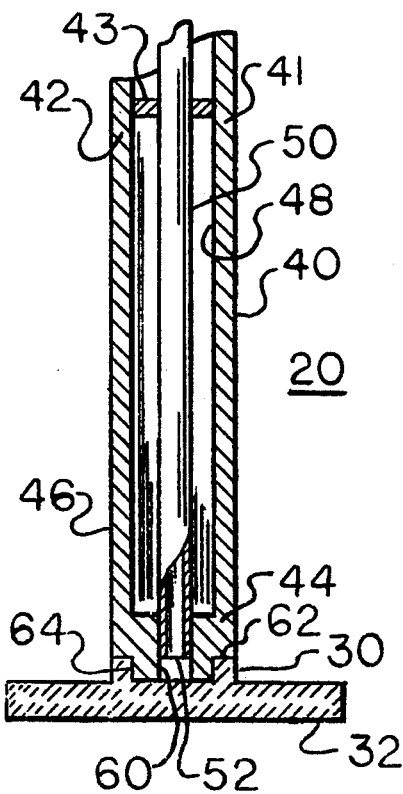
FIG. 2 is a cross-sectional view of a probe.

In FIG. 2, there is shown a probe 20 in accordance with the invention. The probe is comprised of a filter head 30, a cast iron sleeve or tube 40 and a small diameter tube 50.

The filter head can be fabricated from a material selected from porous carbon, silicon nitride, titanium diboride, silicon carbide, alumina, zirconia, titania and mullite. By reference to carbon herein is meant to include all types of carbon which can be formed into a porous filter head, including graphite. The porous filter head is required to permit diffusion of gas from the molten metal, yet it must be impervious to the molten metal even when a vacuum as low as 1 Torr is imposed on the filter head. For purposes of determining the amount of hydrogen in molten aluminum, it is preferred that the porous filter head be comprised of carbon.

For purposes of the present invention, the filter head can have a cylindrical shape substantially the same in diameter as cast iron sleeve 40. The filter head may have a flange section 32, preferably circular in shape, extending beyond the periphery of the diameter of cast iron tube 40. The flange has the advantage that it provides greater surface area for contact with the molten metal and thus provides a greater surface area for the gas to diffuse from the molten metal into the probe. This permits the amount of gas in the melt to be determined in a matter of minutes, for example, in one or two minutes. Thus, the greater surface area of the filter head aids in providing a faster response time for the analyzer.

Figure 4:
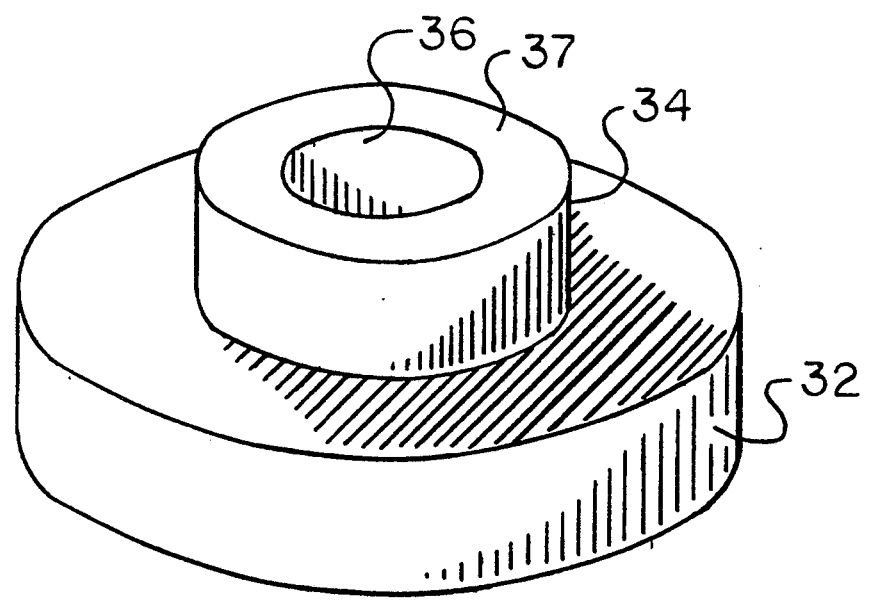
FIG. 4 is a perspective view of an improved porous member.

In the filter head configuration shown in FIG. 4, flange 32 is provided with a collar 34 having an inside cylindrical wall 36 which fits snugly over cast iron sleeve or tube 40, as described below.

In accordance with the invention, the probe further comprises a cast iron tube or sleeve 40 which protects and permits the use of small diameter tube 50 which is essential to the present invention in order to shorten response time.

Figure 3:
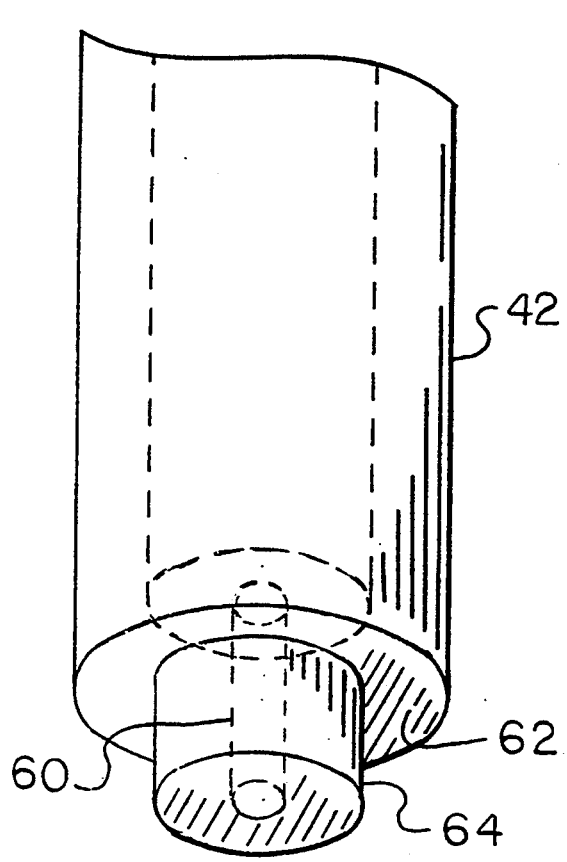
FIG. 3 is a view showing the configuration of the lower portion of the cast iron sleeve.

Cast iron tube or sleeve 40, as shown in FIGS. 2 and 3, is comprised of an upper portion 42 and lower portion 44. Upper portion 42 and lower portion 44 can have a generally cylindrical outside wall 46. Further, upper portion 42 can have a generally cylindrical inside wall 48 which is spaced away from small diameter tube 50. At top or upper end 41 of upper portion 42, a spacer 43 can be provided to fasten or fix small diameter tube 50 in upper portion 42 of cast iron sleeve 40. The spacer can be fabricated out of any material resistant to the operating temperatures.

Lower portion 44 is designed to provide a snug fit with small diameter tube 50. Thus, lower portion 44 is solid except for a cylindrical opening 60 provided therein. Opening 60 is sized so as to provide a fit around small diameter tube 50 which does not permit leakage of air or gas that may be present in the space between upper portion 42 and small diameter tube 50. Thus, small diameter tube 50 is sealed in cylindrical opening 60.

For purposes of providing a connection between filter head 30 and lower portion 44, lower portion 44 is provided with a shoulder 62 and a recessed cylindrical part 64 having a diameter approximately the same as the diameter of inside cylindrical wall 36 of collar 34. Both shoulder 62 and top 37 of collar 34 should have a finish sufficiently smooth to prevent leakage of molten metal therebetween from the melt. Both lower portion 44 and collar 34 can be machined to provide a press fit which prevents leakage.

When the use of the analyzer is, for example, to determine the amount of hydrogen in molten aluminum, it is preferred that the filter head be formed from porous carbon such as porous graphite. Further, sleeve or tube 40 is formed from cast iron, preferably a cast iron which contains 2 to 4.5 wt. % carbon. For best results, the cast iron should contain a saturation amount of carbon, for example, 3 to 4 wt. % carbon for an alloy containing 2% silicon. By cast iron as used herein is meant an iron base alloy containing 0.3 to 5 wt. % silicon, 0.2 to 1.5 wt. % manganese, 0.05 to 0.5 wt. % copper, and 2 to 4.5 wt. % carbon, the remainder incidental elements and impurities. Cast iron is important because it permits the use of graphite without deterioration of the porous filter head. That is, the carbon in the filter does not diffuse into or react with the cast iron to form iron carbide in an amount which causes deterioration of the filter head. When the cast iron has a saturation amount of carbon, then very little, if any, diffusion of carbon into or reaction with the cast iron occurs. Thus, the probe assembly has the advantage that it can be used for long times without deterioration of the carbon filter head. In addition, the cast iron sleeve provides for a rugged probe which can be used repeatedly without concern for thermal shock and the erroneous reading which can result from leaks developing from the thermal shock.

In a preferred embodiment, small diameter tube 50 is fabricated from a stainless steel, such as alloys 316, 304, and 308 or a mild steel such as alloy 1010, and 1018. When a steel is used, it is preferred that tube 50 has its end 52 located or spaced from carbon filter head 32 substantially as shown in FIG. 2. The spacing should be an amount or distance sufficient to resist diffusion from the carbon filter head into the steel comprising tube 50. Copper is another metal that may be used for small diameter tube 50.

For purposes of the present invention, in order to minimize response time, it is preferred that small diameter tube have an inside diameter in the range of 0.010 to 0.080 inch. Typically, the small diameter tube has an outside diameter in the range of 0.05 to 0.25 inch.

Figure 5:
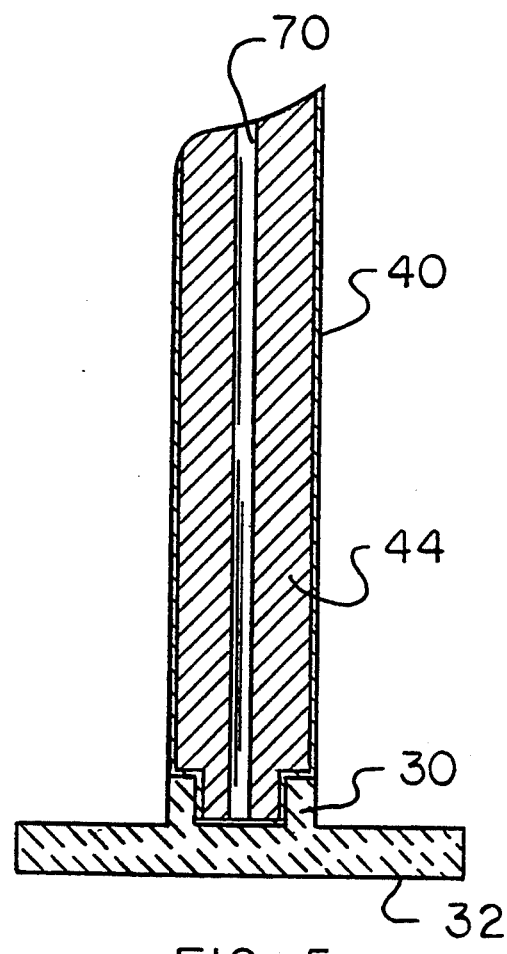
FIG. 5 is a cross-sectional view of a hollow cast iron probe.

It will be appreciated that in FIG. 5 cast iron tube 40 may be fabricated with a central bore 70 instead of a small diameter tube. The diameter of the bore can be similar to that for the inside diameter tube. The cast iron tube having a small central bore is used on a less preferred basis because the small bore can be difficult to fabricate, particularly when it is desired to use a probe several inches in length, for example 9 to 10 inches long.

When the analyzer is used to measure gases in certain molten metals, such a magnesium, for example, the cast iron sleeve is resistant to attack by the molten metal. However, in certain melts, such as molten aluminum, the cast iron can be attacked by the melt. Thus, in a preferred embodiment, a ceramic coating is applied to the cast iron tube. A ceramic coating is chosen that can withstand attack by the particular melt in which it is used. For example, if the analyzer is to be used with molten aluminum, then the cast iron sleeve or tube should be provided with a protective coating of ceramic or vitreous enamel, for example. The ceramic coating suitable for use in molten aluminum is selected from alumina, silicon nitride, titanium diboride, silicon carbide, zirconia, titania, mullite or a combination of these materials. The coatings may be applied by means which provide a continuous coating that adheres to the cast iron surface. Fluxes or additions to lower the melting point of the ceramic may also be incorporated in to the coating For example, such coatings may be applied as a slurry coating and then baked to produce the ceramic outer coating resistant to the molten aluminum. One such coating which can be used in accordance with the invention is available from Consolidated Ceramics Products, Inc., 838 Cherry Street, Blanchester, Ohio 45107. The thickness of the coating can range from 0.003 to 0.05 inch.

In the invention, the small diameter tube is connected to vacuum system 12.

In operation, the probe is lowered into the melt and then a vacuum is drawn on the small diameter tube by vacuum means 12. The vacuum is drawn to a low level, e.g. less than about 0.5 Torr. The vacuum removes any gas present inside the small diameter tubing and inside the pores of the filter head. When molten aluminum is being tested and the porous filter head is graphite, a vacuum of 0.5 Torr is suitable. Then, the vacuum means is turned off and valve 13 is closed to maintain a constant volume inside the evacuated measuring system. After the gas in the melt reaches equilibrium in the small diameter tube or constant volume measuring system, the gas pressure in the small diameter tube is measured. The pressure can be measured by means of a pressure transducer. A suitable transducer is available from Barksdale Controls Division of IMO Industries, 3211 Fruitland Ave., Los Angelas, Calif. 90058. However, other pressure measuring devices can be used, including ion pumps, vacuum gauges, etc.

In another aspect of the invention, a process has been developed for greatly shortening the time required to determine the level of gas presure in molten metal. In accordance with this aspect of the invention, when the probe is first immersed in molten metal, an instantaneous gas pressure, P, is obtained and the rate of gas pressure increase with time, dP/dt, in the evacuated probe is obtained. Thereafter, a doping gas is introduced to the probe to artificially increase the gas pressure therein and then the rate or gas pressure increase, dP/dt, inside the probe is measured again. This procedure may be repeated a number of times until the equilibrium pressure of the gas in the molten metal is reached. In accordance with this aspect of the invention, the equilibrium pressure can be reached much more quickly because this new method does not require the full time for the gas in the probe to build up from the molten metal. That is, only sufficient time is required to determine whether the equilibrium pressure has been reached. This may be done in one or two measurements or in a series of measurements.

Figure 6:
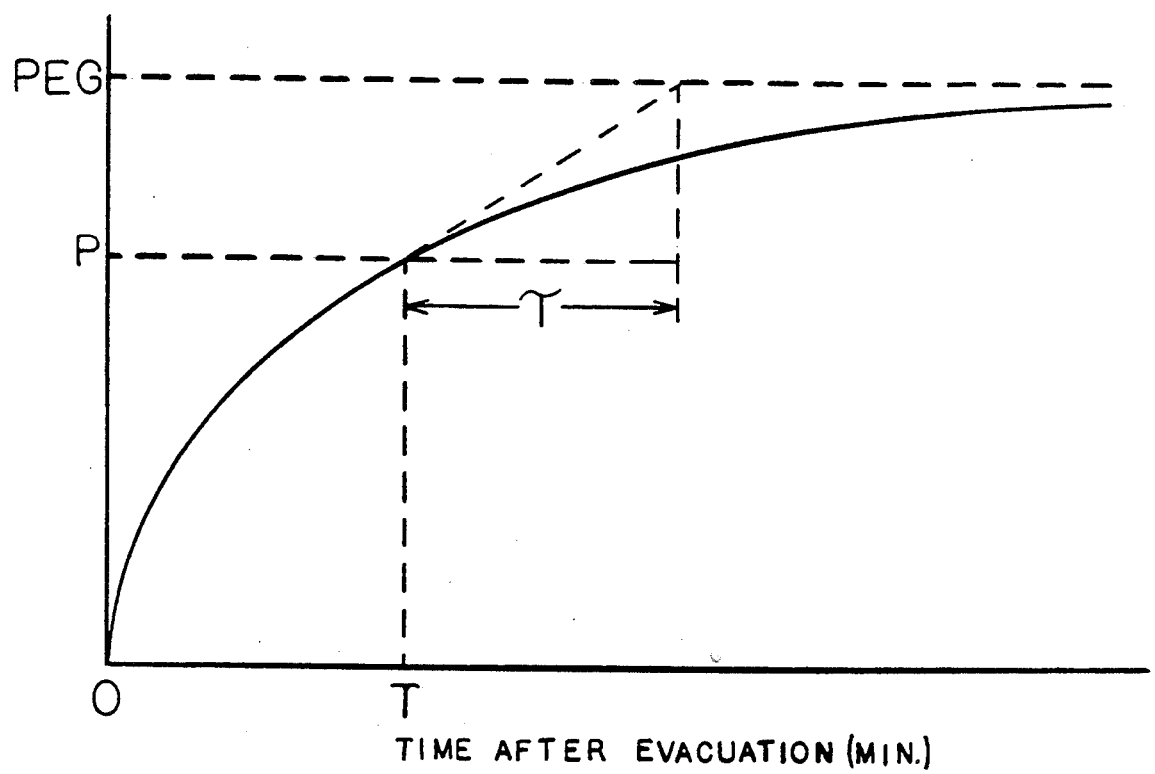
FIG. 6 is a graph showing gas pressure change with time.

The importance of using a doping gas can be seen from FIG. 6 which illustrates how the gas pressure would increase with time without doping. At time zero (when valve 13 closes) the pressure is at its lowest point after evacuation. If it is assumed that the rate of gas transfer (in moles/minute) from the molten metal into the evacuated probe is proportional to the difference between the equilibrium pressure and internal probe pressure (Peq-P), then it is possible to derive the following relationship:

$$\frac{P}{Peq} = 1 - \exp^{-t/\tau} \qquad (1)$$

where P is the instantaneous measured gas pressure (in Torr) at any time; Peq is the equilibrium gas pressure (in Torr), t is the time of the pressure measurement (min.); and $\tau$ is a time constant of the measuring system. The time constant depends on the internal volume of the measurement system and the permeability of the porous filter medium 30. Equation (1) means that when $t=\tau$, the pressure P will be 0.632 times the value of Peq.

When $t=2\tau$, P will be 0.86 times Peq, and when $t=3\tau$, P will be 0.95 times Peq. It is also possible to take the time derivative of equation (1) to calculate the rate of change of pressure:

$$\frac{dP}{dt} = \frac{Peq}{\tau} \exp^{-t/\tau} \quad (2)$$

By combining equations (1) and (2) and rearranging the terms, Peq is defined as follows:

$$Peq = P + \tau \frac{dP}{dt} \quad (3)$$

The significance of equation (3) is obtained by examining the straight line drawn tangent to the pressure curve given in FIG. 6. The slope of the line tangent to the pressure curve is equal to dP/dt. Following this line out a distance $\tau$ gives the equilibrium pressure. This is true at any point on the pressure curve.

Figure 7:
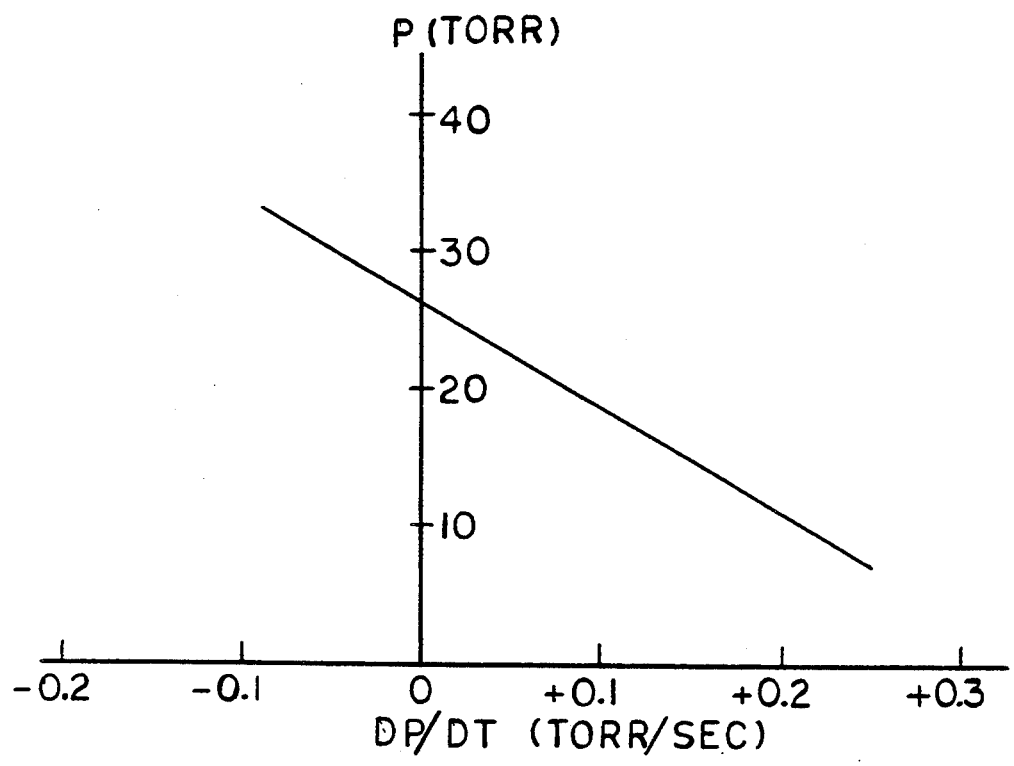
FIG. 7 is a graph showing the rate of pressure change with total pressure in the melt.

Another consequence of equation 3 is that the difference between the equilibrium and actual pressures, Peq-P, is proportional to the rate of change of pressure, dP/dt. This means that as the equilibrium approached the rate of pressure increase, dP/dt, becomes small and an extremely long time is required to reach a true equilibrium value. However when doping is employed both the rate of pressure change with time, dP/dt, and the actual pressure can be measured. This can be done after doping to a number of different pressures, and the results plotted as shown in FIG. 7.

By use of this relationship, it is not necessary to wait for equilibrium to occur. It is possible to predict the equilibrium pressure from the instantaneous gas pressure P and to calculate the rate of pressure increase, dP/dt at the same time. The time constant of the measurement system must be known. An example of the results obtained by a series of six gas dopings, followed by pressure measurements, is given in FIG. 7. Note that when the gas pressure P inside the measurement volume is greater than the equilibrium pressure (about 600 Tort in this case), then the valve of dP/dt becomes negative. That is, the pressure P decreases with time t because gas is now diffusing from the probe into the liquid metal. At the region near equilibrium (that is, near dP/dt=0), there is a linear relationship between P and dP/dt. In practice, it is sufficient to take a linear interpolation at two points near dP/dt=0.

A computer based algorithm was developed using equation (3) and a doping and interpolation scheme as described above, to make a series of gas measurements in the aforementioned 356 alloy. Multiple readings were taken with the results: 0.118, 0.1109, 0.101, 0.0997, 0.0971, 0.1075, 0.118, 0.109, 0.084 and 0.105 cc/100 g. The average of these eleven readings is 0.105±0.008 cc/100 g. These readings were obtained in less than 2 minutes.

EXAMPLE

The data presented below were obtained in melts of aluminum alloy AA 356 (Al-7% Si-0.3% Mg) held at about 750 to 770C. A probe assembly was employed that consisted of a cast iron sleeve 40 and a porous graphite disc 32 as shown in FIG. 2. The cast iron sleeve 40 contained a 316 stainless steel tube having an inner diameter of 0.03 inch and an outer protective oxide layer to prevent dissolution of cast iron in the bath. The probe measurement volume was evacuated by connecting to a vacuum means, and then closing off the measurement volume by closing valve 13. During evacuation and measurement, doping valve 6 is closed and valve 15 to pressure measuring device 14 is opened. Once a suitable low pressure, e.g., 0.5 Torr is obtained, valve 13 is closed. The pressure inside the measurement volume is recorded with time by pressure measuring device 14, and the rate of change of pressure, dP/dt, and the pressure P are calculated and recorded. Then the doping valve is opened for a few seconds to increase the pressure, and afterwards P and dP/dt are recorded once more. The doping and measurements are repeated until the pressure P becomes greater than the equilibrium pressure. The results obtained are tabulated below:

| Measured Pressure (Torr) | Rate of Change in Pressure, dP/dt (Torr/sec) |
|---|---|
| 8.2 | 0.256 |
| 10.7 | 0.20 |
| 24.5 | 0.038 |
| 34.8 | −0.084 |

The results are also plotted in FIG. 7. It is seen that the equilibrium pressure is about 28 Torr, which corresponds to a gas content of 0.17 cc/100 g in this alloy.

While the invention has been set forth with respect to preferred embodiments, all embodiments are claimed which come within the spirit of the invention.

What is claimed is:

1. A hollow probe for immersion in a molten metal for determining the gas content thereof by drawing a vacuum on the probe and permitting gas to permeate from the molten metal and equilibrate in the probe wherein gas pressure can be measured to determine the gas pressure in the molten metal, the probe comprising:
   (a) a porous filter head permeable to gas in said molten metal and impermeable to said molten metal;
   (b) a hollow cast iron sleeve having an upper portion and a lower portion, the sleeve attached to said filter head at the lower portion; and
   (c) a small diameter tube positioned in said sleeve, said tube having a first end extending to said lower portion of said sleeve adjacent to said filter head, said tube having a second end attached to one of means for drawing a vacuum on said tube and means for measuring gas pressure in said tube.

2. The probe in accordance with claim 1 wherein said cast iron sleeve has a ceramic coating thereon resistant to attack by molten metal.

3. The probe in accordance with claim 1 wherein said small diameter tube has an inside diameter in the range of 0.01 to 0.08 inch.

4. The probe in accordance with claim 1 wherein said small diameter tube is fabricated from a material selected from ceramic material and metal.

5. The probe in accordance with claim 1 wherein said small diameter tube is fabricated from steel.

6. The probe in accordance with claim 1 wherein small diameter tube is fabricated from stainless steel.

7. The probe in accordance with claim 1 wherein said lower portion of said sleeve has a cylindrical shaped shoulder section and said filter head has a cylindrical recessed section for fitting snugly to said cylindrical shoulder section.

8. The probe in accordance with claim 1 wherein said porous filter head is fabricated from a material selected from at least one of the group consisting of carbon, silicon nitride, titanium diboride, silicon carbide, alumina, zirconia, titania and mullite.

9. The probe in accordance with claim 1 wherein said porous filter head is fabricated from carbon.

10. A hollow probe for immersion in a molten metal for determining the gas content thereof by drawing a vacuum on the probe and permitting gas to permeate from the molten metal and equilibrate in the probe wherein gas pressure can be measured to determine the gas pressure in the molten metal, the probe comprising:

(a) a porous filter head permeable to gas in said molten metal and impermeable to said molten metal;

(b) a cast iron tube having an upper portion and a lower portion, the tube attached to said filter head at the lower portion, said tube having a second end attached to one of means for drawing a vacuum on said tube and means for measuring gas pressure in said tube.

11. The probe in accordance with claim 10 wherein said cast iron tube has a ceramic coating thereon resistant to attack by molten metal.

12. The probe in accordance with claim 10 wherein said cast iron tube has an inside diameter in the range of 0.01 to 0.1 inch.

13. A hollow probe for immersion in a molten metal for determining the gas content thereof by drawing a vacuum on the probe and permitting gas to permeate from the molten metal and equilibrate in the probe wherein gas pressure can be measured to determine the gas pressure in the molten metal, the probe comprising:

(a) a porous carbon filter head permeable to gas in said molten metal and impermeable to said molten metal;

(b) a hollow cast iron sleeve having an upper portion and a lower portion, the sleeve having a ceramic coating thereon resistant to attack by said molten metal, the sleeve attached to said filter head at the lower portion; and (c) a small diameter stainless steel tube having an outer diameter in the range of 0.05 to 0.25 inch and positioned in said sleeve, said tube having a first end extending to said lower portion of said sleeve adjacent to said filter head, said tube having a second end attached to one of means for drawing a vacuum on said tube and means for measuring gas pressure in said tube.

14. A method for determining the level of gas in a molten metal comprising the steps of:

(a) providing a probe having a porous portion in a molten metal, the porous portion permeable to gas in said molten metal and impermeable to said molten metal, the probe connected to one of a doping gas, a vacuum system and a gas pressure measuring device;

(b) providing a vacuum in said probe;

(c) holding said probe under vacuum for a period sufficient for gas in said molten metal to pass through said porous portion into said probe to provide a measurable gas pressure in said probe;

(d) thereafter, measuring said gas pressure to establish rate of gas pressure change as said gas passes through said porous portion into said probe and to establish an average gas pressure during said period;

(e) adding a controlled amount of said doping gas to said probe thereby increasing gas pressure in said probe by a controlled amount;

(f) repeating step (d) to reach by extrapolation a gas pressure in equilibrium with the gas pressure in said molten metal; and (g) calculating the equilibrium gas pressure to determine the level of gas in said melt.

15. The method in accordance with claim 14 wherein steps (d) and (e) are repeated until the gas pressure in said probe is equal to or greater than the gas pressure in said molten metal.

16. The method in accordance with claim 14 wherein the metal is molten aluminum and said gas is hydrogen gas.

* * * * *